United States Patent [19]

Plath et al.

[11] 4,340,739

[45] Jul. 20, 1982

[54] N-HALOMETHYLANILIDES

[75] Inventors: Peter Plath, Ludwigshafen; Karl Eicken, Wachenheim; Wolfgang Rohr, Mannheim, all of Fed. Rep. of Germany

[73] Assignee: BASF Aktiengesellschaft, Fed. Rep. of Germany

[21] Appl. No.: 99,018

[22] Filed: Nov. 30, 1979

[30] Foreign Application Priority Data

Dec. 18, 1978 [DE] Fed. Rep. of Germany ....... 2854599

[51] Int. Cl.$^3$ ................. C07D 261/08; C07D 263/32; C07D 367/30; C07D 333/12

[52] U.S. Cl. ................................. 548/236; 546/245; 548/265; 548/341; 549/73; 560/31; 564/162; 564/167; 564/182; 564/183; 564/192

[58] Field of Search .............. 548/235, 236, 248, 265, 548/341; 260/247.3; 546/245; 549/70, 73; 560/31; 564/162, 167, 182, 183, 192

[56] References Cited

U.S. PATENT DOCUMENTS

| | | | |
|---|---|---|---|
| 3,630,716 | 12/1971 | Olin | 71/118 |
| 3,637,847 | 1/1972 | Olin | 260/562 B |
| 3,714,299 | 1/1973 | Olin | 260/926 |
| 3,810,981 | 5/1974 | Olin | 424/204 |
| 4,235,928 | 11/1980 | Eicken et al. | 548/236 |

FOREIGN PATENT DOCUMENTS

| | | |
|---|---|---|
| 1542950 | 4/1972 | Fed. Rep. of Germany . |
| 2119518 | 10/1972 | Fed. Rep. of Germany . |
| 1078071 | 8/1967 | United Kingdom . |
| 1078072 | 8/1967 | United Kingdom . |
| 1350528 | 4/1974 | United Kingdom . |

*Primary Examiner*—Anton H. Sutto
*Attorney, Agent, or Firm*—Keil & Witherspoon

[57] ABSTRACT

Novel valuable N-chloromethyl-carboxylic acid anilides, a process for their preparation, and their use for the preparation of novel valuable N-carboxylic acid anilides.

2 Claims, No Drawings

N-HALOMETHYLANILIDES

The present invention relates to novel valuable N-chloromethyl-carboxylic acid anilides, a process for their preparation, and their use for the preparation of novel valuable N-carboxylic acid anilides.

The adduct formation of acid chlorides, eg. chloroacetyl chloride, cyclopropanecarboxylic acid chloride, methoxyacetyl chloride or 2,4-dichlorobenzoyl chloride with Schiff bases, eg. 2,6-diethyl-N-methylene-aniline or 2-methylene-6-tert.-butyl-N-methylene-aniline, to give the corresponding N-chloromethyl-carboxylic acid anilides, is known; the latter compounds are valuable intermediates for the preparation of known active ingredients of herbicides or insecticides (U.S. Pat. Nos. 3,714,299, 3,810,981, 3,630,716 and 3,637,847, and German Laid-Open Application DOS No. 1,542,950).

Furthermore, N-aryl-N-chloromethyl-carbamates have been obtained by reacting paraformaldehyde, thionyl chloride and N-arylcarbamates in a conventional manner (German Laid-Open Application DOS No. 2,119,518), and the said DOS emphasizes that such products are only obtainable by the processes disclosed in the DOS, but not by adduct formation of O-aryl esters of chlorocarbonic acid with trimerized Schiff bases [hexahydrotriazines].

Though the adduct formation of, for example, benzoyl chloride with N-methylene-2,6-dimethylaniline is claimed in U.S. Pat. Nos. 3,630,716 and 3,637,847, the literature contains nothing on the compound N-chloromethyl-2,6-dimethyl-N-benzoylaniline which is the expected product of this reaction. The situation is similar with other N-chloromethyl-carboxylic acid anilides, which, though claimed, are not substantiated by Preparation Examples or by information in the description.

We have found that compounds of the general formula:

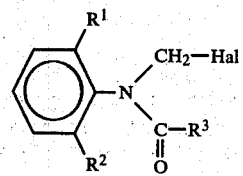

where $R^1$ is methyl, ethyl, isopropyl, methoxy or chlorine, $R^2$ is methyl, ethyl, isopropyl or chlorine, $R^3$ is unsubstituted or halogen-substituted benzyl or 1-phenylethyl, or is phenyl which is unsubstituted or is monosubstituted or disubstituted by methyl, fluorine, chlorine, bromine, iodine, cyano, trifluoromethyl, nitro, methoxy or methylthio, or is a 5-membered or 6-membered heterocyclic radical which is unsubstituted or substituted by methyl or chlorine and possesses one or two identical or different hetero-atoms selected from the group comprising oxygen, sulfur and nitrogen, or is —CH$_2$—Y or

where Y is $C_1$–$C_4$-alkylthio or is phenoxy or phenylthio which are unsubstituted or are monosubstituted or polysubstituted by chlorine, fluorine, methyl, trifluoromethyl or nitro, or $R^3$ is —X—$R^4$, where X is oxygen or sulfur and $R^4$ is phenyl which is unsubstituted or is monosubstituted or disubstituted by fluorine, chlorine, bromine, trifluoromethyl, $C_1$–$C_4$-alkyl, nitro, methoxy or methylthio, and Hal is fluorine, chlorine or bromine, are valuable intermediates for the preparation of valuable novel N-carboxylic acid anilides.

Further, we have found that the N-halomethyl-N-arylcarboxylic acid anilides are obtained when a substituted N-methylene-aniline of the formula:

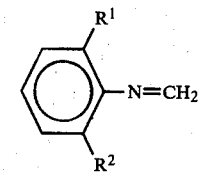

is reacted with a carboxylic acid halide of the formula $R^3$—CO—Hal in a solvent, Hal, $R^1$, $R^2$ and $R^3$ having the above meanings. This reacton is contrary to the disclosure of German Laid-Open Application DOS No. 2,119,518.

Further, we have found that compounds of the formula:

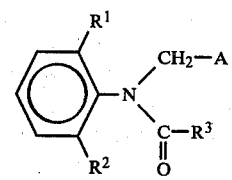

where $R^1$, $R^2$ and $R^3$ have the above meanings and A is a pyrazole, imidazole or 1,2,4-triazole radical, each of which may be unsubstituted or monosubstituted or polysubstituted by methyl, ethyl, isopropyl, chlorine, bromine or nitro, are obtained when an N-halomethyl-carboxylic acid anilide of the formula:

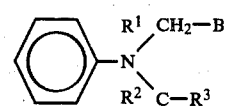

where $R^1$, $R^2$, $R^3$ and Hal have the above meanings, is reacted with an azole of the formula A-M, where A has the above meanings and M is hydrogen, potassium or sodium, in the presence or absence of a diluent or of an acid acceptor or of both.

The novel compounds may be prepared as follows:

If 2,6-dimethyl-N-methylene-aniline and 2-furoyl chloride are used as starting materials, the course of the reaction can be represented by the following equation:

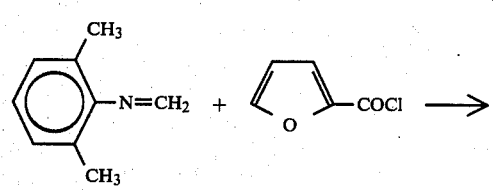

-continued

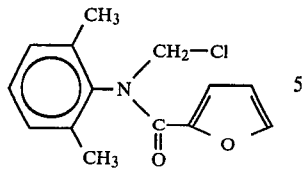

In the formulae, R¹ and R² are preferably methyl, ethyl or isopropyl, and R³ is preferably phenyl, benzyl, 1-phenylethyl, 2-chloro-α-phenylethyl, 2-methylphenyl, 3-methylphenyl, 4-methylphenyl, 2-chlorophenyl, 3-chlorophenyl, 4-chlorophenyl, 2-fluorophenyl, 3-fluorophenyl, 4-fluorophenyl, 3-bromophenyl, 2-iodophenyl, 2,6-difluorophenyl, 3-cyanophenyl, 2-nitrophenyl, 3-nitrophenyl, 4-nitrophenyl, 3-trifluoromethylphenyl, 4-trifluoromethylphenyl, 3-methoxyphenyl, 4-methylthiophenyl, 2,3-dichlorophenyl, 2,4-dichlorophenyl, methylthiomethyl, phenylthiomethyl, phenoxymethyl, 2,4-dichlorophenoxymethyl, thien-2-yl, thienyl-3-yl, fur-2-yl, fur-3-yl, 2,5-dimethyl-fur-3-yl, 4-chlorothien-3-yl, 2-chloropyrid-3-yl, 2,6-dichloropyrid-4-yl, 3-methylisoxazol-5-yl, 4-methyl-oxazol-5-yl, phenoxy, 2,4-dichlorophenoxy, 2,3-dichlorophenoxy, 4-nitrophenoxy, 3,5-dimethoxyphenoxy, 4-isopropylphenoxy, 4-tert.-butylphenoxy, 3-methylphenoxy and 4-methylthiophenoxy.

The Schiff bases to be used as starting materials may be prepared by conventional methods (cf. U.S. Pat. No. 3,637,847) from paraformaldehyde and anilines in toluene. The carboxylic acid chlorides also required as starting materials are either well-known laboratory chemicals or can be synthesized by methods known from the literature. The azoles A-M (where M=H) are conventional compounds well-known in organic chemistry.

Preferred diluents for the reactions according to the invention are toluene, naphtha or n-hexane. However, solvents such as acetonitrile or dimethylformamide may also be used for the preparation of the azole compounds or cyanamide compounds.

Acid acceptors which may be used are inorganic acid acceptors, for example alkali metal carbonates, eg. sodium carbonate, or tertiary amines, eg. triethylamine or pyridine, or an excess of the azole itself. The reaction temperature may vary from −10° to +150° C. but is preferably from 20° to 120° C.

The N-halomethyl compounds are prepared using, for example, 1 mole of carboxylic acid halide per mole of Schiff base. The compounds may be isolated by, for example, filtration or concentration.

To prepare the azole compounds, preferably from 1 to 2 moles of the azole A-M and 1 mole of acid acceptor are employed per mole of the N-halomethyl compound.

The azole compounds may be isolated by, for example, filtering the reaction mixture, washing the filtrate with water, and drying and concentrating it. If desired, the crude product obtained may be purified by recrystallization.

The chemical Examples which follow illustrate the invention:

EXAMPLE 1

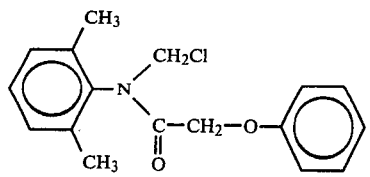

A solution of 26.6 g (0.2 mole) of N-methylene-2,6-dimethylaniline in 100 ml of toluene is slowly added dropwise, at 0°-5° C., to a solution of 34.1 g (0.2 mole) of phenoxyacetyl chloride in 50 ml of naphtha. After stirring the mixture for 16 hours at room temperature, the product which has precipitated is filtered off. After drying under reduced pressure, 47 g (78%) of N-chloromethyl-2,6-dimethyl-phenoxyacetanilide, of melting point 87° C., are obtained.

EXAMPLE 2

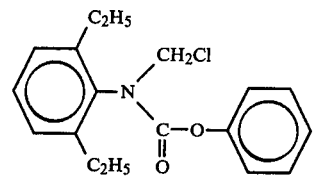

A solution of 32.2 g (0.2 mole) of N-methylene-2,6-diethylaniline in 50 ml of naphtha is added to a solution of 31.3 g (0.2 mole) of phenyl chloroformate in 100 ml of naphtha at 15°-20° C., with slight cooling. After stirring the mixture for 16 hours at room temperature, and filtering off and drying the product, 49.2 g (76%) of N-chloromethyl-N-2,6-diethylphenyl-carbamic acid O-phenyl ester, of melting point 94°-95° C., are obtained.

EXAMPLE 3

315 parts by volume of a toluene solution which contains 1 mole of 2,6-dimethyl-phenylazomethine, prepared as described in U.S. Pat. No. 3,637,847, are added dropwise, whilst stirring, to a solution of 130.5 parts by weight of 2-furanecarboxylic acid chloride in 100 parts by volume of toluene at 5°-10° C., whilst cooling, and stirring is then continued for 10 hours at room temperature. After cooling the mixture, filtering off the product and drying it under reduced pressure, 198 parts by weight of N-chloromethylfuran-2-carboxylic acid 2',6'-dimethylanilide, of melting point 124°-126° C., are obtained.

The following compounds, where Hal=Cl, are obtained similarly.

| No. | R¹ | R² | R³ | M.p. (°C.) |
|---|---|---|---|---|
| 1 | CH₃ | CH₃ | benzyl | 62-64 |
| 2 | CH₃ | CH₃ | CH₂—S—CH₃ | crystalline mass |
| 3 | CH₃ | C₂H₅ | " | 127 |
| 4 | C₂H₅ | C₂H₅ | " | oil |
| 5 | CH₃ | CH₃ | CH₂—O—⟨phenyl⟩ | 87 |
| 6 | C₂H₅ | C₂H₅ | " | |

-continued

| No. | R¹ | R² | R³ | M.p. (°C.) |
|---|---|---|---|---|
| 7 | CH₃ | CH₃ | CH₂—O—[phenyl-Cl,Cl] | 122-125 |
| 8 | C₂H₅ | C₂H₅ | " | 98-99 |
| 9 | CH₃ | CH₃ | CH₂—O—[phenyl-Cl] | |
| 10 | CH₃ | CH₃ | CH₂—S—[phenyl] | |
| 11 | CH₃ | CH₃ | CH₂—S—[cyclohexyl-Cl] | |
| 12 | CH₃ | CH₃ | —CH(CH₃)—[phenyl] | |
| 13 | C₂H₅ | C₂H₅ | —CH(CH₃)—[phenyl] | $n_D^{23} = 1.5547$ |
| 14 | C₂H₅ | C₂H₅ | —CH(CH₃)—[cyclohexyl-Cl] | |
| 15 | CH₃ | CH₃ | " | |
| 16 | CH₃ | CH₃ | phenyl | 133 |
| 17 | C₂H₅ | C₂H₅ | phenyl | 98-99 |
| 18 | C₃H₇—i | C₃H₇—i | " | 107-108 |
| 19 | CH₃ | CH₃ | 2-methylphenyl | 118-119 |
| 20 | CH₃ | CH₃ | 3-methylphenyl | 133-135 |
| 21 | CH₃ | CH₃ | 4-methylphenyl | 119-120 |
| 22 | CH₃ | CH₃ | 2-chlorophenyl | 93 |
| 23 | CH₃ | CH₃ | 3-chlorophenyl | 145 |
| 24 | CH₃ | CH₃ | 4-chlorophenyl | 126 |
| 25 | CH₃ | CH₃ | 2-fluorophenyl | 86-88 |
| 26 | CH₃ | CH₃ | 3-fluorophenyl | 114-115 |
| 27 | CH₃ | CH₃ | 4-fluorophenyl | 141-143 |
| 28 | CH₃ | CH₃ | 3-cyanophenyl | 116-118 |
| 29 | C₂H₅ | C₂H₅ | 3-cyanophenyl | 112-114 |
| 30 | CH₃ | CH₃ | 2-nitrophenyl | 205-207 |
| 31 | C₂H₅ | C₂H₅ | 2-nitrophenyl | |
| 32 | CH₃ | CH₃ | 3-nitrophenyl | 152-154 |
| 33 | C₂H₅ | C₂H₅ | 4-nitrophenyl | 118-120 |
| 34 | C₂H₅ | C₂H₅ | 3-CF₃—phenyl | 63-64 |
| 35 | CH₃ | CH₃ | 4-CF₃—phenyl | 108-109 |
| 36 | C₂H₅ | C₂H₅ | 2,4-dichlorophenyl | 68-69 |
| 37 | CH₃ | CH₃ | 2,4-dichlorophenyl | 108 |
| 38 | CH₃ | CH₃ | fur-2-yl | 124-126 |
| 39 | C₂H₅ | C₂H₅ | fur-2-yl | 69-70 |
| 40 | CH₃ | CH₃ | fur-3-yl | |
| 41 | CH₃ | CH₃ | 3,5-dimethylfuryl | used directly as a solution |
| 42 | CH₃ | CH₃ | thien-2-yl | 94-97 |
| 43 | CH₃ | CH₃ | thien-3-yl | used directly as a solution |
| 44 | CH₃ | CH₃ | 4-chlorothien-3-yl | 118 |
| 45 | C₃H₇—i | C₃H₇—i | thien-2-yl | 94-95 |
| 46 | C₃H₇—i | C₃H₇—i | 2,6-difluorophenyl | 135 |
| 47 | CH₃ | CH₃ | 3-methylisoxazol-5-yl | 106 |
| 48 | CH₃ | CH₃ | 4-methyl-oxazol-5-yl | 83-85 |
| 49 | CH₃ | CH₃ | phenoxy | 113-115 |
| 50 | CH₃ | CH₃ | —S—[phenyl] | |
| 51 | C₂H₅ | C₂H₅ | " | |
| 52 | C₂H₅ | C₂H₅ | 2,4-dichlorophenoxy | |
| 53 | C₂H₅ | C₂H₅ | 2-methyl-4-chlorophenoxy | |
| 54 | CH₃ | C₂H₅ | 4-nitrophenoxy | |
| 55 | C₂H₅ | C₂H₅ | 4-isopropyl-phenoxy | |
| 56 | C₂H₅ | C₂H₅ | 4-tert.-butylphenoxy | |
| 57 | C₃H₇—i | C₃H₇—i | phenoxy | 115-116 |

The novel N-halomethyl-carboxylic acid anilides are valuable products which can be further converted, by simple methods, to valuable N-azolylmethyl-carboxylic acid anilides which possess a surprising fungicidal action which is also, surprisingly, superior to that of similar compounds.

The Examples which follow illustrate the preparation of these compounds.

EXAMPLE 4

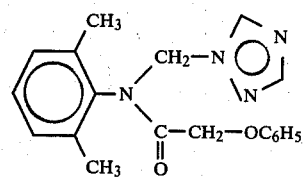

10.7 g (155 millimoles) of 1,2,4-triazole are suspended in 100 ml of toluene and 23.5 g (77.5 millimoles) of N-chloromethyl-2,6-dimethyl-(phenoxyacet)anilide, prepared as described in Example 1, are added. The reaction mixture is then heated for 1 hour at 130° C. so as to bring it to the boil. When it has cooled, it is filtered, the filter residue is washed with toluene and the filtrate is concentrated. After removing residual toluene, 17 g (65% of theory) of N-1,2,4-triazolylmethyl-N-phenoxyacetyl-2,6-dimethylaniline, of melting point 84° C., are obtained.

EXAMPLE 5

20 g (63 millimoles) of N-chloromethyl-N-2,6-diethylphenyl-carbamic acid O-phenyl ester (Example 2) in 100 ml of toluene are mixed with 8.6 g (126 millimoles) of imidazole; the reaction mixture is then boiled for 1 hour, and filtered whilst still hot. The oil which remains after concentrating the filtrate crystallizes on triturating with naphtha. After filtering off the product and drying it, 13.9 g (63% of theory) of N-imidazol-1-yl-methyl-N-2,6-diethylphenyl-carbamic acid O-phenyl ester, of melting point 115°–116° C., are obtained.

EXAMPLE 6

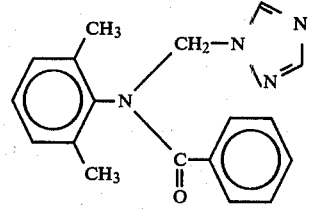

C₁₈N₁₈N₄O (a) 140.5 g (1 mole) of benzoyl chloride are dissolved in 200 ml of naphtha and a solution of 133 g (1 mole) of N-methylene-2,6-dimethylaniline in toluene is then added dropwise at 5°–10° C. After stirring the mixture for 14 hours at 25° C., the solid which has precipitated is isolated by filtration and is dried under reduced pressure, giving 215 g (79%) of N-chloromethyl-N-benzoyl-2,6-dimethylaniline of melting point 133° C.; formula:

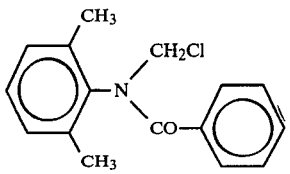

N-Chloromethyl-N-benzoyl-2,6-diethylaniline, of melting point 98°–99° C., was obtained similarly.

(b) A solution of 54.7 g (0.2 mole) of N-chloromethyl-N-benzoyl-2,6-dimethylaniline in 250 ml of tetrahydrofuran is added dropwise, at 5°–10° C., to a suspension of 13.8 g (0.2 mole) of triazole in 100 ml of tetrahydrofuran and 20.2 g (0.2 mole) of triethylamine. After stirring for 16 hours at room temperature (25° C.), the triethylammonium hydrochloride which has separated out is filtered off. After stripping off the solvent, the solid isolated from the filtrate is dissolved in 250 ml of CH$_2$Cl$_2$ and the solution is extracted by shaking with 100 ml of 5 percent strength by weight hydrochloric acid. The organic phase is dried over Na$_2$SO$_4$ and then concentrated; the residue left is recrystallized from a 3:2 toluene/naphtha mixture.

44.6 g (73%) of N-(triazolylmethyl)-N-benzoyl-2,6-dimethylaniline of the formula:

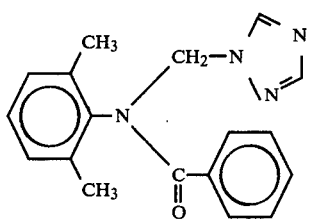

are obtained; melting point 135° C.

N-(Triazolylmethyl)-N-benzoyl-2,6-diethylaniline was prepared similarly; melting point 112°–115° C.

EXAMPLE 7

(a)

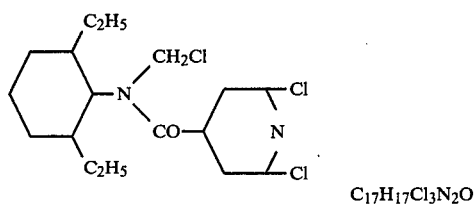

C$_{17}$H$_{17}$Cl$_3$N$_2$O 38.6 g (0.24 mole) of N-methylene-2,6-diethylaniline are added dropwise to a solution of 51.4 g (0.24 mole) of 2,6-dichloro-pyridine-4-carboxylic acid chloride in 250 ml of toluene. The reaction temperature is kept at 35°–40° C. by cooling in a waterbath. After stirring the mixture for 10 hours, the toluene is stripped off under reduced pressure on a rotary evaporator and the residue left is stirred thoroughly with naphtha. After filtering off the product and drying it, 67 g (75%) of the N-chloromethylanilide of the above structure are obtained; melting point 79°–80° C.

(b)

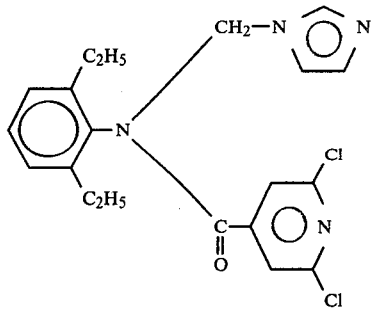

A mixture of 22.3 g (0.06 mole) of the above N-chloromethylanilide and 9 g (0.132 mole) of imidazole in 100 ml of toluene is refluxed for 1 hour and then filtered hot. A solid is isolated from the filtrate after cooling and is recrystallized from a 1:1 mixture of naphtha and toluene. Yield after recrystallization: 11 g (46%); melting point: 120°–122° C.

The novel N-azolylmethyl-carboxylic acid anilides prepared using the novel N-halomethyl-carboxylic acid anilides exhibit a powerful fungitoxic activity against phytopathogenic fungi, especially of the class of the Phycomycetes. The compounds may therefore be used, for example, for combating *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in vines, *Plasmopara halstedii* in sunflowers, *Sclerospora macropora* in Indian corn, *Bremia lactucae* in lettuce, *Mucor mucedo* in fruit and *Rhizopus nigricans* in beets. The fungicidal agents which contain these compounds contain from 0.1 to 95% by weight, preferably from 0.5 to 90% by weight, of active ingredient. The amounts used vary, depending on the desired effect, from 0.1 to 5 kg of active ingredient per hectare. Some of the active ingredients exhibit curative properties. ie. they can be used even after infection of the plants by the pathogen, in order to be certain of success in controlling the latter. Furthermore, many of the novel compounds have a systemic action, so that it is also possible to protect visible parts of the plants by a root treatment. The fungicidal action of these compounds is surprisingly superior to that of the conventional fungicides.

Furthermore, the compounds may also be used against fungi which cause seedling diseases and germination diseases, for example species of Pythium and Aphanomyces in leguminosae and cotton. The amounts used are from 10 to 200 g of active ingredient per 100 kg of seed; the materials are applied in the form of seed dressings.

We claim:

1. A compound of the general formula

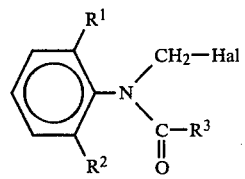

where $R^1$ is methyl, ethyl, isopropyl, methoxy or chlorine, $R^2$ is methyl, ethyl, isopropyl or chlorine, $R^3$ is a 5-membered or 6-membered heterocyclic radical selected from the group consisting of thien-2-yl, thienyl-3-yl, fur-2-yl, fur-3-yl, 2,5-dimethylfur-3-yl, 4-chlorothien-3-yl, 2-chloropyrid-3-yl, 2,6-dichloropyrid-4-yl, 3-methylisoxazol-5-yl or 4-methyl-oxazol-5-yl, or is —CH$_2$Y or

where Y is $C_1$–$C_4$-alkylthio or is phenoxy or phenylthio which are unsubstituted or are monosubstituted or polysubstituted by chlorine, fluorine, methyl, trifluoromethyl or nitro, or $R^3$ is —X—$R^4$, where X is oxygen or sulfur and $R^4$ is phenyl which is unsubstituted or is monosubstituted or disubstituted by fluorine, chlorine, bromine, trifluoromethyl, $C_1$–$C_4$-alkyl, nitro, methoxy or methylthio, and Hal is fluorine, chlorine or bromine.

2. A compound selected from the group comprising

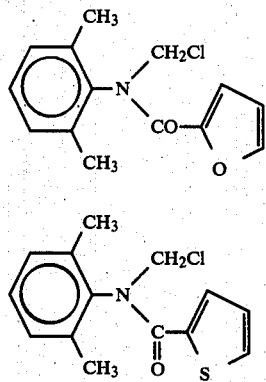

-continued

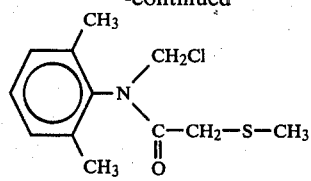

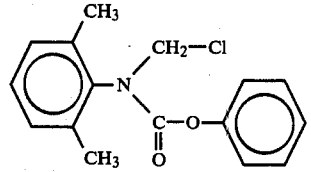

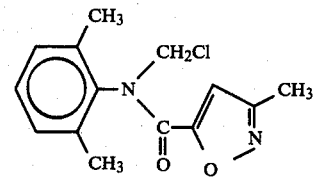

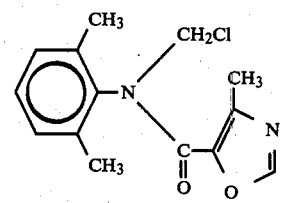

and

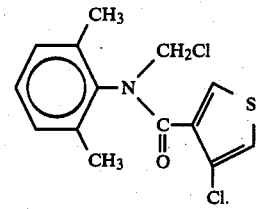

* * * * *